(12) United States Patent
Crowe et al.

(10) Patent No.: US 8,641,707 B2
(45) Date of Patent: Feb. 4, 2014

(54) MEDICAL DEVICE HAVING A BIMATERIAL VALVE

(75) Inventors: John E. Crowe, Menlo Park, CA (US); John W. Sliwa, Los Altos, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1695 days.

(21) Appl. No.: 11/647,303

(22) Filed: Dec. 29, 2006

(65) Prior Publication Data
US 2008/0161785 A1  Jul. 3, 2008

(51) Int. Cl.
*A61B 18/18* (2006.01)
(52) U.S. Cl.
USPC ................................. 606/41; 607/38
(58) Field of Classification Search
USPC .............. 604/99.04, 101.05; 606/38–39
See application file for complete search history.

(56) References Cited

U.S. PATENT DOCUMENTS

| | | | |
|---|---|---|---|
| 5,899,218 A | 5/1999 | Dugan | |
| 6,017,338 A | 1/2000 | Brucker et al. | |
| 6,083,170 A | 7/2000 | Ben-Haim | |
| 6,425,853 B1 | 7/2002 | Edwards | |
| 6,645,202 B1 | 11/2003 | Pless et al. | |
| 6,652,515 B1 * | 11/2003 | Maguire et al. | 606/41 |
| 6,689,128 B2 | 2/2004 | Sliwa, Jr. et al. | |
| 6,701,931 B2 | 3/2004 | Sliwa, Jr. et al. | |
| 6,719,755 B2 | 4/2004 | Sliwa, Jr. et al. | |
| 6,805,128 B1 | 10/2004 | Pless et al. | |
| 6,805,129 B1 | 10/2004 | Pless et al. | |
| 6,840,936 B2 | 1/2005 | Sliwa, Jr. et al. | |
| 6,858,026 B2 | 2/2005 | Sliwa, Jr. et al. | |
| 6,971,394 B2 | 12/2005 | Sliwa, Jr. et al. | |
| 7,052,493 B2 | 5/2006 | Vaska et al. | |
| 2002/0045895 A1 * | 4/2002 | Sliwa et al. | 606/41 |
| 2005/0000577 A1 | 1/2005 | Alman et al. | |
| 2005/0171527 A1 * | 8/2005 | Bhola | 606/41 |
| 2006/0084966 A1 | 4/2006 | Maguire et al. | |
| 2006/0184121 A1 | 8/2006 | Brockman et al. | |

OTHER PUBLICATIONS

International Search Report and Written Opinion of the International Searching Authority for PCT/US07/88424 dated Jul. 1, 2008.

\* cited by examiner

*Primary Examiner* — Linda Dvorak
*Assistant Examiner* — Jaymi Della
(74) *Attorney, Agent, or Firm* — Wiley Rein LLP (57) ABSTRACT

Medical devices using fluid or cooling fluids having one or more bimaterial valves positioned at each point of flow control to control the flow of a fluid in response to temperature changes. In particular, devices for ablating tissue having multiple ablation elements or cells include one or more bimaterial valves positioned within or near the ablation cells. The bimaterial valves respond to temperature changes by adjusting the flow rate of a fluid through the valve.

13 Claims, 8 Drawing Sheets

MEDICAL DEVICE HAVING A BIMATERIAL VALVE

BACKGROUND OF THE INVENTION a. Field of the Invention

The instant invention generally relates to medical devices incorporating one or more bimaterial valves to provide fluid control and methods for using the devices for treatments that benefit from device fluid perfusion or device cooling fluids. In particularly preferred embodiments, the instant invention relates to devices and methods for treating electrophysiological diseases of the heart, such as epicardial ablation for the treatment of atrial fibrillation. More generally, the present invention relates to devices and methods for the improved delivery of a flowable material to a target tissue.

b. Background Art

In performing a number of minimally invasive procedures, such as cardiac ablation of an epicardial tissue, it is desirable to maintain or control the tissue at an appropriate temperature to avoid undesirable thermal damage. A flowable material, such as saline, may be used to cool or temperature-control tissue and to maintain adequate acoustic contact between an acoustic ablation device and a tissue. The source of flowable material can be an intravenous bag of saline in which the flow is gravity driven or a positive displacement pump. For medical devices having multiple internal points of flow control, for example ablation devices having multiple ablation cells or elements, fluid may flow to each ablation cell at approximately the same rate in both an unpowered "standby" mode and in a powered ablating mode. However, in practice, the ablation cells may be activated in phases such that some cells are active while others are inactive. Enough coolant must be provided to all cells simultaneously as if all are operating. Further, if some cells tend to operate hotter than others, there is no mechanism for maintaining a peak temperature across all cells other than decreasing the power to the hotter cells. It would be desirable to be able to selectively deliver a larger amount of coolant to an individual cell so that each cell could more efficiently deliver the needed ablation and still remain below a peak design temperature.

A disadvantage of the existing devices and procedures is that the flow rate of a fluid to the individual cells is not individually controlled or adjustable. It is therefore desirable to provide devices and methods having individual flow rate control at the level of each cell based on temperature changes to allow for higher flow rates to active cells and lower flow rates to inactive cells.

BRIEF SUMMARY OF THE INVENTION

The present invention meets these and other objectives by providing devices having one or more bimaterial valves incorporated at each point of flow control and methods of using same. In particularly preferred embodiments, the devices and methods will utilize one or more bimaterial valves integrated at each ablation cell or element of a multi-cell ablation device such that the flow rate of a fluid to individual cells may be self-adjusted based on local temperature changes.

According to one embodiment, the devices of the present invention include at least one fluid lumen and at least one ablation cell connected to the at least one fluid lumen. Each ablation cell includes an ablation element and a fluid passageway. The device also includes a bimaterial valve positioned along the fluid passageway of the at least one ablation cell such that a flow rate of a fluid flowing from the fluid lumen to the ablation cell or cells increases as the temperature of the ablation cell(s) or an adjacent tissue increases. Alternatively, the bimaterial valve may be positioned along the at least one fluid lumen. The ablation elements may be high intensity focused ultrasound elements.

The bimaterial valve preferably comprises a first material having a first thermal expansion coefficient and a second material having a second thermal expansion coefficient bonded to the first material. The first thermal expansion coefficient is preferably greater than the second thermal expansion coefficient. In preferred embodiments, the first material of the bimaterial valve comprises copper and the second material comprises nickel. Alternatively, the second material may comprise steel, aluminum, brass, gold, iron or platinum.

The bimaterial valve may be positioned such that it has an initial flow rate of R1 when the temperature is T1 and has an increased flow rate of R2 when the temperature increases to T2. The bimaterial valve may optionally comprise a third material having a third thermal expansion coefficient. The first, second and third materials are positioned with respect to each other such that the bimaterial valve has an initial flow rate of R1 when the temperature is T1 and has an increased flow rate of R2 when the temperature increases to T2. The bimaterial valve may further comprise a fourth material having a fourth thermal expansion coefficient, wherein the first, second, third and fourth materials are positioned with respect to each other such that the bimaterial valve has an initial flow rate of R1 when the temperature is T1 and has an increased flow rate of R2 when the temperature increases to T2. In one embodiment, R1 is zero.

The bimaterial valve may include a thermally expandable or deformable element that will lay substantially flat when the temperature is below a predetermined temperature and will form a gap through which a fluid may flow when the temperature rises above a predetermined temperature. The expandable element may be a flap that deflects with an increase in temperature to increase a flow rate of the valve. The initial flow rate may be zero.

The device may optionally include a membrane enclosing the ablation element of the at least one ablation cell. The membrane and the ablation element define a fluid chamber therebetween. The membrane preferably includes at least one duct through which a fluid may flow or weep. The device may include a plurality of ablation cells and either a single fluid lumen connecting to the plurality of ablation cells or a plurality of fluid lumens, wherein each fluid lumen connects to a single ablation cell.

According to another embodiment, the devices of the present invention include a catheter comprising a catheter body having a fluid lumen and at least one bimaterial valve positioned along the fluid lumen. The at least one bimaterial valve includes a first material having a first thermal expansion coefficient and a second material having a second thermal expansion coefficient bonded or fused to the first material. The first and second materials are chosen such that at least one expandable element on the valve will remain substantially closed or will restrict flow when the temperature is below a predetermined temperature and will form a gap through which a fluid may flow when the temperature rises above a predetermined temperature. The expandable element may be a flap or cantilever element that deflects with an increase in temperature to increase a flow rate of the valve.

The first thermal expansion coefficient is preferably greater than the second thermal expansion coefficient. The bimaterial valve may optionally include a third material having a third thermal expansion coefficient. The first, second and third materials are positioned with respect to each other such that the bimaterial valve has an initial flow rate of R1 when the temperature is T1 and has an increased flow rate of R2 when the temperature increases to T2. Typically R1 will be greater than zero, but a flow rate of zero is also within the scope of the invention.

In another aspect of the invention, a method of ablating cardiac tissue from an epicardial location includes the steps of providing an ablation device comprising at least one fluid lumen, at least one ablation cell having an ablation element and a fluid passageway, and at least one bimaterial valve positioned along the fluid passageway of the ablation cell, and connecting a fluid source to said ablation device such that the at least one bimaterial valve may control or modify the flow rate of a fluid in response to changes in temperature. The method may further include responding to an increasing temperature of the ablation cell or an adjacent tissue by increasing the flow rate of a fluid through the passageway and/or responding to a decreasing temperature of the ablation cell or an adjacent tissue thereby decreasing the flow rate of a fluid through the passageway. The responding is done by the self-acting deforming bimaterial valve in response to temperature changes.

In still another aspect of the invention, a method of controlling the flow of a fluid includes the steps of providing a catheter or scope comprising a catheter body having a fluid lumen and at least one bimaterial valve, and connecting a fluid source to said catheter or scope such that the at least one bimaterial valve may control the flow rate of a fluid in response to changes in temperature. The method may further include the steps responding to an increasing temperature by increasing the flow rate of a fluid through the passageway and/or responding to a decreasing temperature by decreasing the flow rate of a fluid through the passageway.

In yet another aspect of the invention, a method of manufacturing an ablating device having a bimaterial valve includes providing a first material, the first material having a first thermal expansion coefficient, bonding or fusing a second material to the first material, the second material having a second thermal expansion coefficient, creating a deformable flap in the first and second materials thereby creating a bimaterial valve, providing an ablating device having at least one ablation cell, each ablation cell having an ablation element and a fluid passageway, and attaching the bimaterial valve to the fluid passageway of the at least one ablation cell such that the flap in the bimaterial valve may deflect as the temperature of the ablation cell increases thereby increasing a flow rate of a fluid in the fluid passageway. The deformable flap may be created by etching, stamping or laser-cutting. The first thermal expansion coefficient is preferably greater than the second thermal expansion coefficient. The first material may comprise copper and the second material may comprise nickel, aluminum, brass, steel, gold, iron or platinum The method may optionally comprise the step of bonding a third material to the first material, the third material having a third thermal expansion coefficient. Optionally still, the method may comprise the step of bonding a fourth material to the third material, the fourth material having a fourth thermal expansion coefficient. The attaching step may include snap-assembling or fitting the bimaterial valve within the fluid passageway.

In another aspect of the invention, a method of manufacturing a catheter or scope having a bimaterial valve includes the steps of providing a first material, the first material having a first thermal expansion coefficient, bonding a second material to the first material, the second material having a second thermal expansion coefficient, creating a flap in the first and second materials thereby creating a bimaterial valve, providing a catheter or scope having a body, the catheter or scope body having a lumen, and attaching the bimaterial valve to the catheter or scope such that the flap in the bimaterial valve deflects as the temperature increases allowing an increased volume of fluid to flow through the bimaterial valve. The attaching step may include positioning the bimaterial valve within the lumen of the catheter or scope body such that the bimaterial valve may restrict the flow of a fluid through the lumen.

One advantage of the present invention is providing individual flow rate control at each ablation cell or element based on local temperature changes allowing for higher flow rates to active cells and lower flow rates to inactive cells.

Another advantage of the present invention is more accurate and controlled delivery of fluid to the target tissue during an ablation procedure, resulting in a decreased risk of overheating or undertreating.

A further advantage of the present invention is greater conservation of a flowable material, such a saline, due to more accurate and controlled delivery of a flowable material to the target tissue and through the individual cells.

An additional advantage of the present invention is more controlled delivery of fluid to a target tissue to provide improved wetted acoustic or thermal coupling to the tissue.

Another advantage of the present invention is providing an inexpensive valve mechanism for flow rate control in a disposable medical device.

The foregoing and other aspects, features, details, utilities, and advantages of the present invention will be apparent from reading the following description and claims, and from reviewing the accompanying drawings.

DETAILED DESCRIPTION OF THE INVENTION

As used herein, the words "preferred," "preferentially," and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention, and no disclaimer of other embodiments should be inferred from the discussion of a preferred embodiment or a figure showing a preferred embodiment.

For purposes of this disclosure, the term "bimaterial valve" means a valve that uses at least two materials having different thermal expansion coefficients. The term "bimaterial valve" is not limited to valves using only two materials, but may include valves using at least three, at least four or more than four materials having different thermal expansion coefficients. The materials are selected such that the bimaterial valve will cause a flow change with changing temperature. The flow change is preferably a monotonic gradual change; however, the flow change may be an abrupt turning-on or shutting-off. The flow change may be an increase or a decrease in the flow rate of a flowable material.

Figure 1:
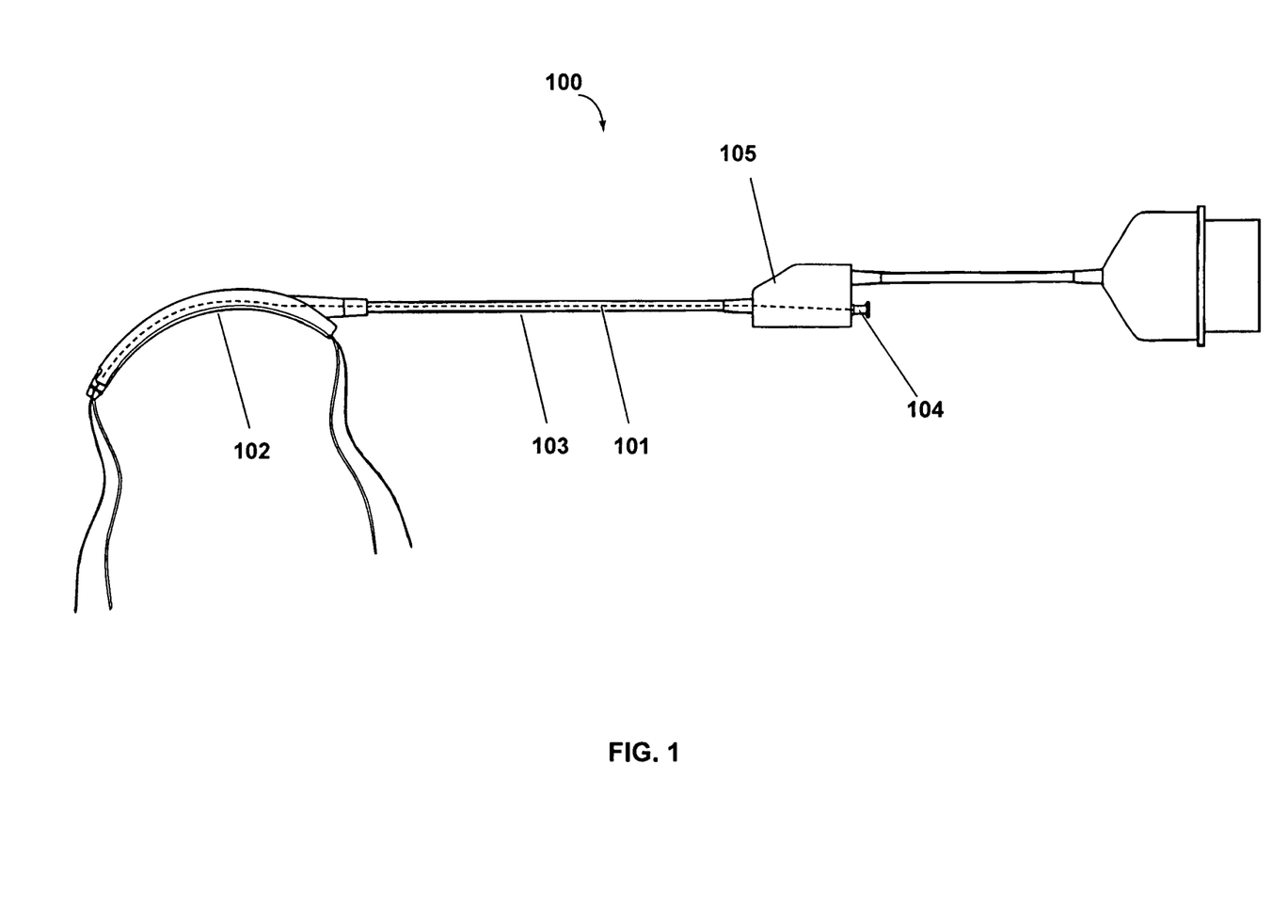
FIG. 1 illustrates an ablation device according to one embodiment of the present invention having a single lumen feeding multiple ablation elements.
Figure 4A:
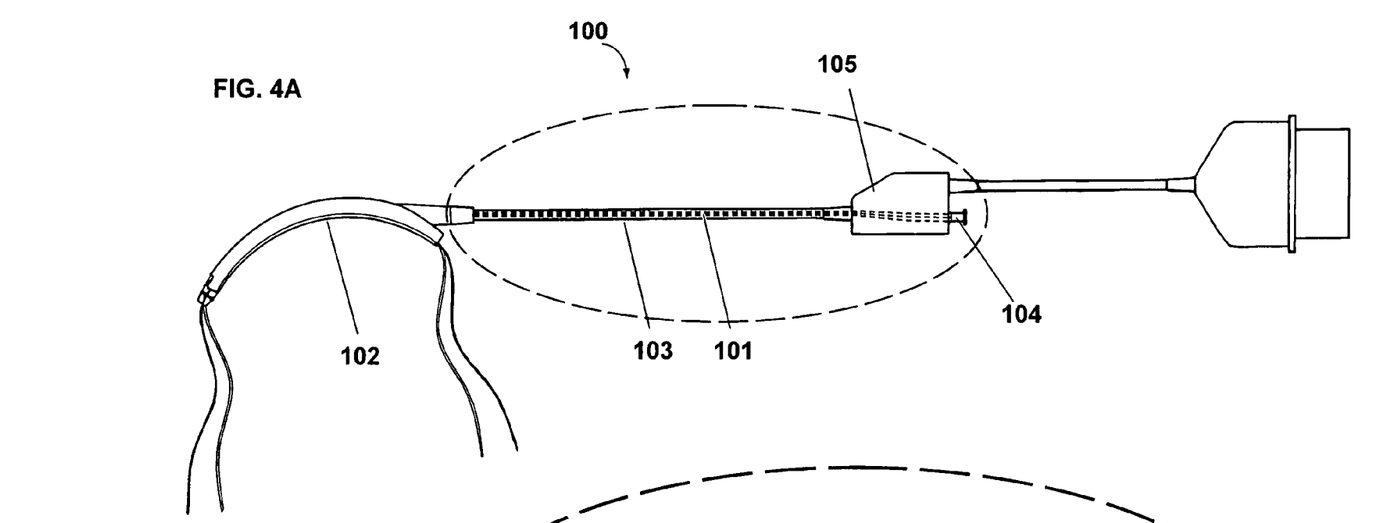
FIG. 4A depicts an ablation device having multiple lumens, each lumen feeding a single ablation cell.
Figure 4B:
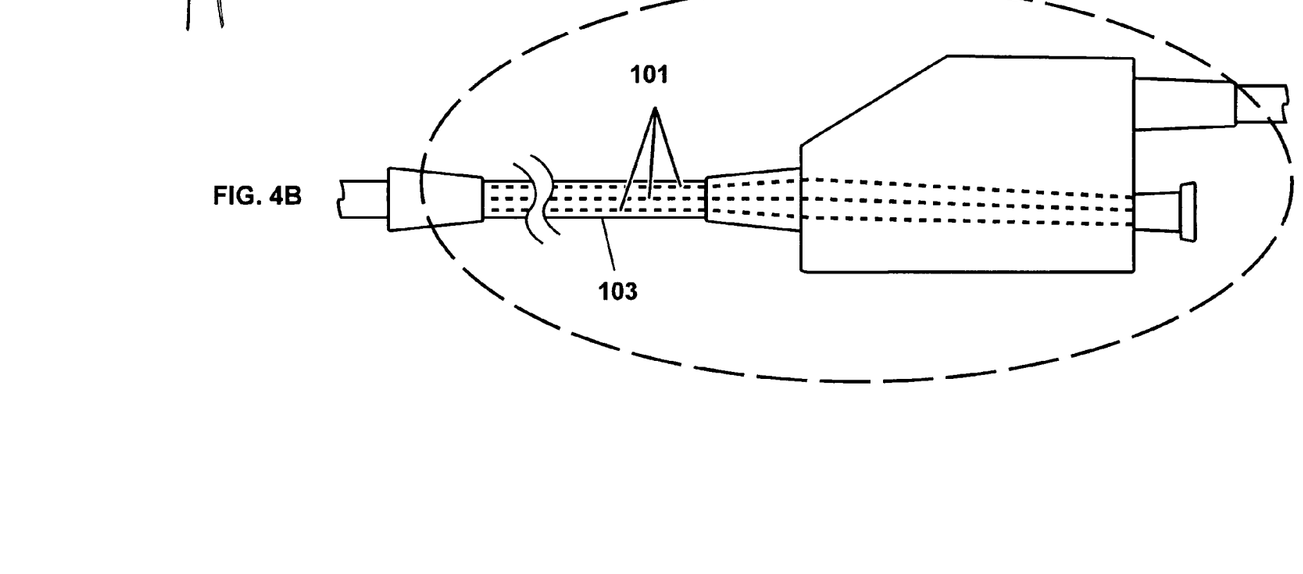
FIG. 4B illustrates an exploded view of the body of the device shown in FIG. 4A.

Referring to FIGS. 1 and 4A-B, an ablation device according to one embodiment of the present invention is shown. The ablation device 100 includes a body having a fluid lumen 101 and a plurality of ablation cells 102 arranged on a curved surface. The fluid lumen 101 may extend from a manifold 105 near the proximal end of the device to the ablation cells 102 near the distal end of the device and may be connected to a source of flowable material via a standard luer connector 104. The body having a fluid lumen 101 is preferably an elongated tube having a lumen for carrying a flowable material, such as saline or hypertonic saline, however the body may have any suitable shape. The body may be enclosed in a casing 103. In another preferred embodiment, the device may have multiple fluid lumens, each fluid lumen being connected to a single ablation cell (FIGS. 4A-B). Alternatively, the device may have multiple fluid lumens and each fluid lumen may be connected to two or more ablation cells. The fluid lumen is preferably made of a biologically acceptable polymeric material, such as silicone, urethane, or polyvinyl chloride (PVC). One of ordinary skill will appreciate, however, that any suitable materials and methods may be used to form the fluid lumen without departing from the spirit and scope of the present invention.

Referring now to FIGS. 2A-B and 3A-B, each ablation cell 102 includes an ablation element 106, a fluid passageway 107 and at least one bimaterial valve. The bimaterial valve 108 is preferably integrated at a location where it may be responsive to temperature changes that cause the valve to deflect or expand and alter flow of a flowable material. A bimaterial valve may be positioned at a location near a target tissue so that it may respond to changes in tissue temperature, or a valve may be positioned away from a target tissue so that it may be more responsive to changes in ablation cell temperature. Alternatively, a bimaterial valve may be positioned at an intermediate location where it may be responsive to both tissue temperature and ablation cell temperature.

Figure 2A:
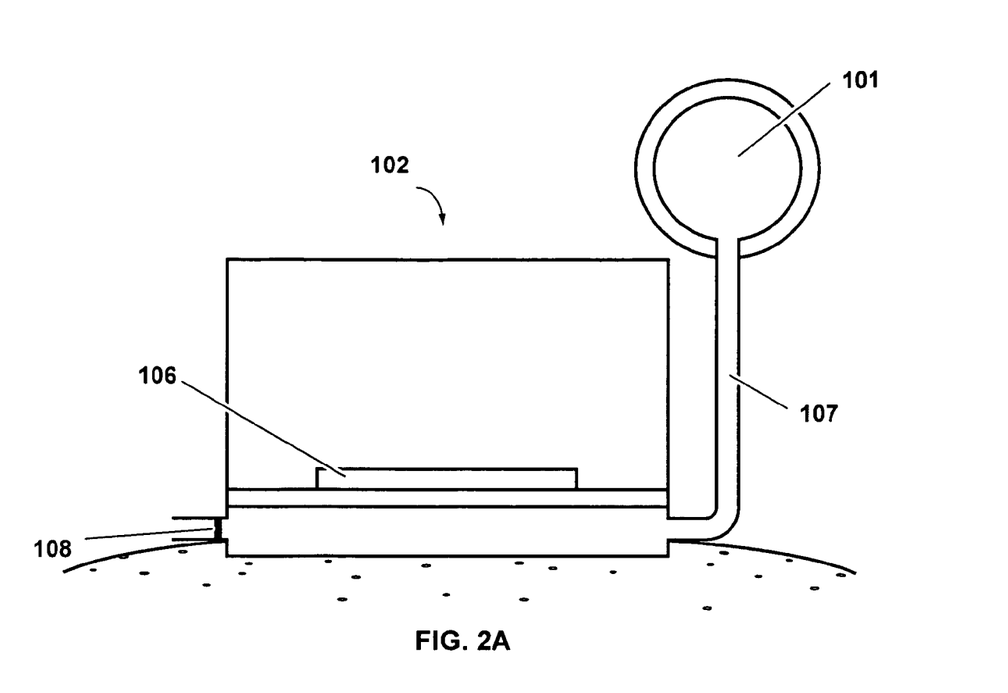
FIG. 2A depicts an ablation cell having a bimaterial valve positioned downstream of an ablation element.
Figure 2B:
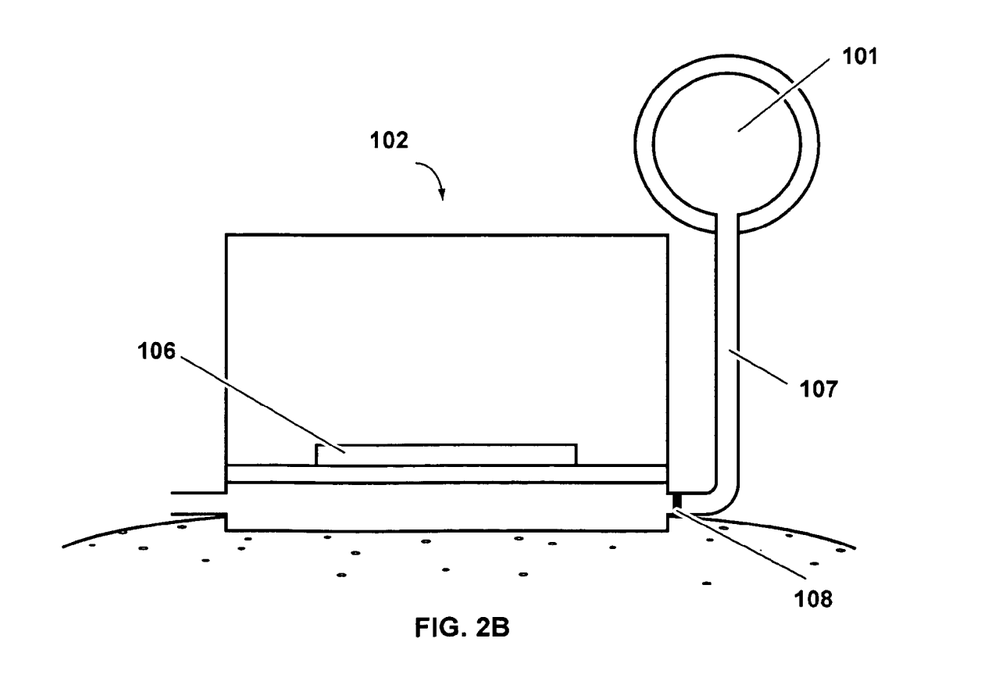
FIG. 2B depicts an ablation cell having a bimaterial valve positioned upstream of an ablation element.
Figure 3A:
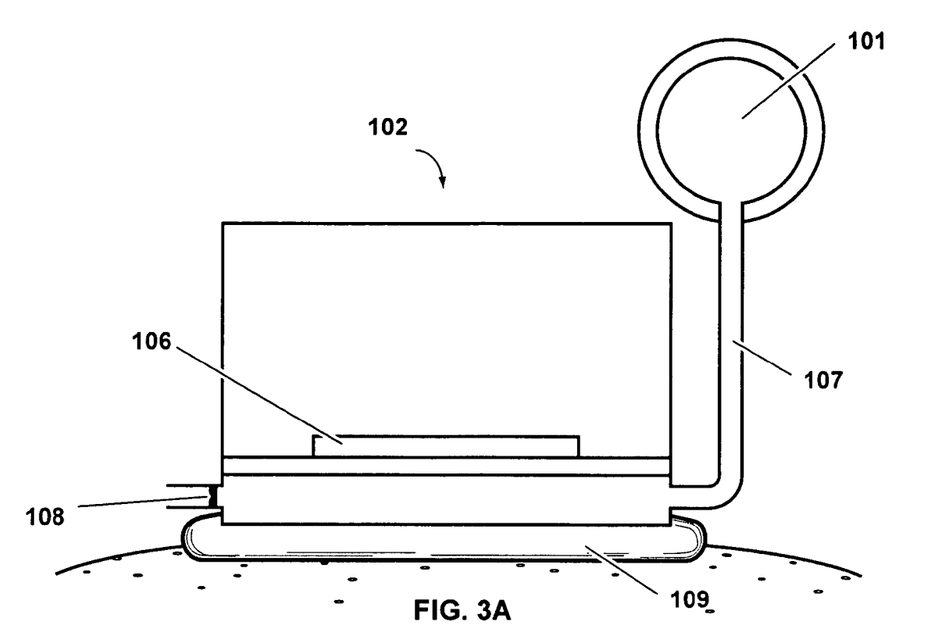
FIG. 3A illustrates the ablation cell of FIG. 2A having a flexible membrane.
Figure 3B:
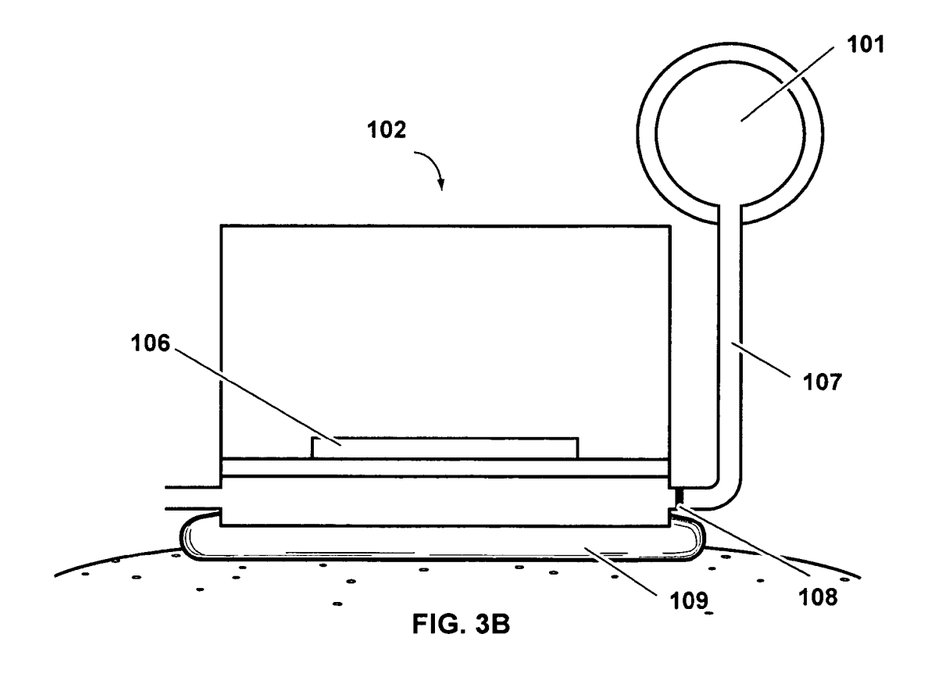
FIG. 3B illustrates the ablation cell of FIG. 2B having a flexible membrane.

In preferred embodiments, a bimaterial valve is integrated into an ablation cell 102 along a fluid passageway 107. The valve may be integrated downstream of an ablation element as shown in FIGS. 2A and 3A, or upstream of an ablation element as shown in FIGS. 2B and 3B. The bimaterial valve is preferably located outside the energy path of the ablation element; however, the valve may be located within the energy path. The bimaterial valve may alternatively be integrated into the fluid lumen 101 near the fluid passageway of an ablation cell 102. A person of skill in the art will appreciate that a bimaterial valve may be integrated at any suitable location where it may respond to temperature changes and cause a change in the flow rate of a flowable material.

The device may include a single bimaterial valve or multiple bimaterial valves located at the same or different positions within the device. For example, the device may include two bimaterial valves, one valve being positioned in the fluid lumen and a second valve being positioned within a fluid passageway of an ablation cell. Alternatively, the device may include two or more bimaterial valves positioned adjacent each other within the device.

The device 100 has at least one ablation element, preferably about 5 to about 30 ablation elements, more preferably about 10 to about 25 ablation elements, and most preferably less than about 15 elements. It should be understood, however, that any number of ablation elements may be used depending upon the specific application for the ablation device. For example, the ablation device may be used to extend around multiple vessels, such as the four pulmonary veins, or only a single vessel, such as the aorta, a pulmonary vein, the superior vena cava, or inferior vena cava, in which case the ablation device preferably includes about 4 to about 12 ablation elements, and more preferably includes about 8 ablation elements. Ablation devices that are suitable for use in accordance with the present invention are described in U.S. Pat. No. 7,052,493 to Vaska, et al. ("Vaska"), which is hereby expressly incorporated by reference as though fully set forth herein. The ablation elements may be arranged in any two-dimensional or three-dimensional configuration. For example, the ablation elements may be aligned in a linear configuration or may be configured in an array having multiple rows of ablation elements aligned side by side.

The ablation elements 106 are preferably focused ultrasound elements, but may be any element for directing and delivering ablating energy to the cardiac tissue, including, but not limited to, radio frequency (RF) elements, laser elements, cryogenic elements and microwave elements. The ablation elements preferably have a width of about 1 mm to about 15 mm, more preferably of about 10 mm, and a length of about 2 mm to about 25 mm, more preferably of about 12 mm. The ablation cells may optionally include a flexible membrane 109 enclosing the ablation element and forming a fluid chamber between the ablation element and the membrane (FIGS. 3A-B). The membrane 109 may include one or more ducts, orifices or pinholes (not shown) through which a fluid may flow or weep. As generally known in the art, a fluid may be used to acoustically couple an ultrasound ablation element to a tissue and to deliver the ultrasonic energy to the tissue.

Figure 5:
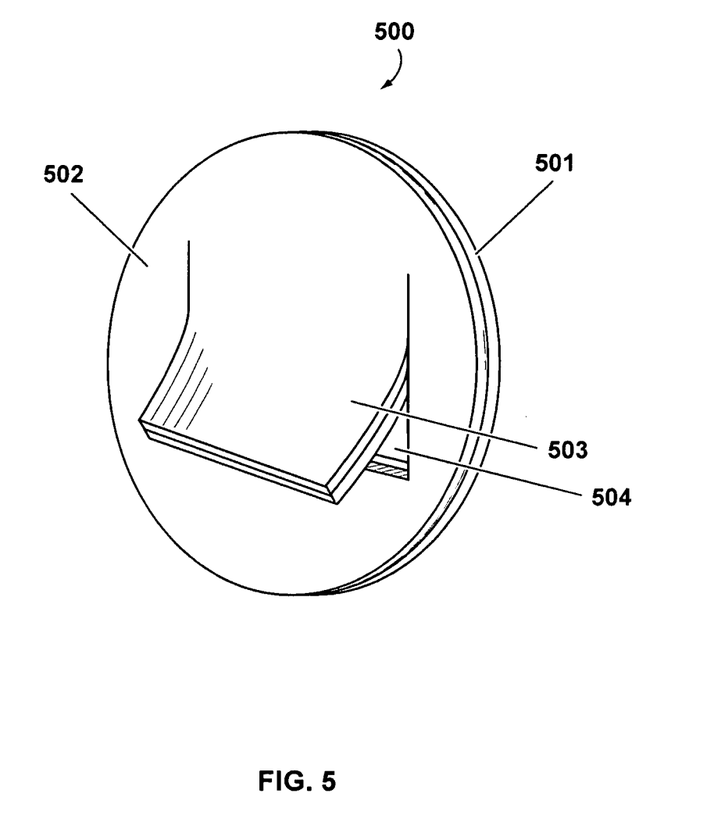
FIG. 5 illustrates an exemplary bimaterial valve.
Figure 6:
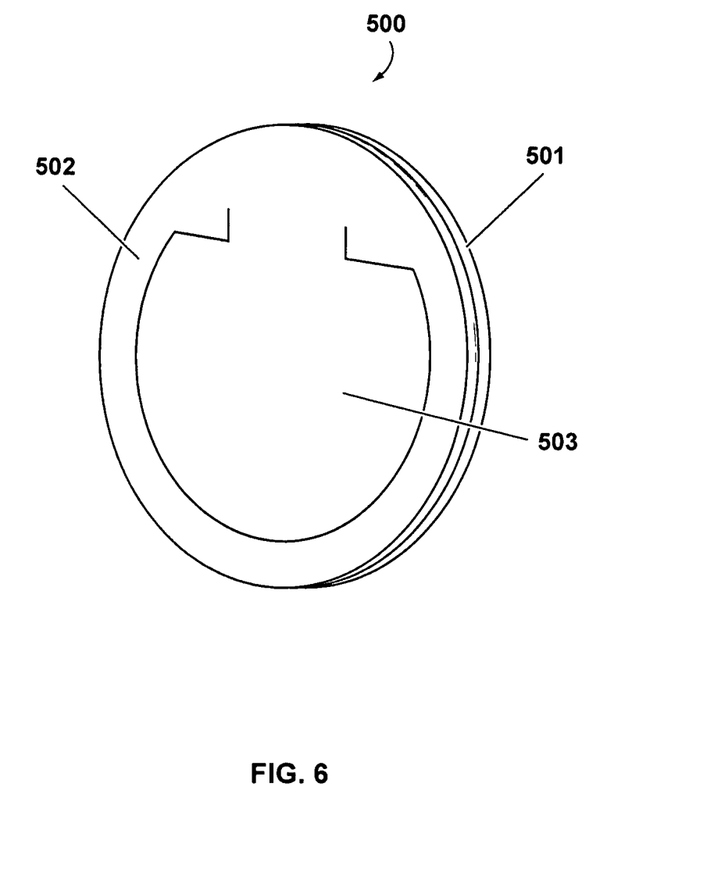
FIG. 6 depicts another exemplary bimaterial valve.

Referring now to FIGS. 5-6, in preferred embodiments, a bimaterial valve 500 usable according to the present invention comprises a first material 501 having a first thermal expansion coefficient and a second material 502 having a second thermal expansion coefficient bonded or fused to the first material 501. The valve 500 includes a single flow orifice 504 that provides a pathway for a flowable material, but valve 500 may include more than one flow orifice. The first 501 and second 502 materials preferably include a thermally movable, deformable or expandable element 503. The movable element is preferably a flap 503 formed from the first and second materials, for example, using etching, stamping or laser-cutting techniques. The flap may have a rectangular shape as shown in FIG. 5 or a more rounded shape as shown in FIG. 6. Alternatively, the movable element may be a separate element (not shown) bonded to the second material 502 and made of the same material as or a different material from the second material. In alternative embodiments, the movable element may be a spiral, a plate, a panel, a paddle or a disc. The valve 500 may include more than one movable element, and the movable elements may operate simultaneously or at different times, depending on the materials chosen and their respective coefficients of thermal expansion.

The movable element may have a closed state and an open state. For example, flap 503 may lay substantially flat in a closed state, and may deflect to form a gap through which a fluid may flow in an open state. It should be understood, however, that the flow rate in a closed state may be greater than zero. In an ultrasonic ablation device, for example, a fluid is necessary to assure acoustic coupling between the ablation elements and the underlying target tissue. Thus, even when flap 503 is in a closed state, some fluid may pass through the valve so that the initial flow rate is greater than zero. In alternative embodiments, the initial flow rate may be zero when flap 503 is in a closed state such that an abrupt turning-on or shutting-off of the fluid flow may be achieved.

A bimaterial valve is preferably integrated along a fluid lumen or within a fluid passageway of an ablation cell such that it may respond to temperature changes and cause a change in the flow rate of a flowable material through the fluid lumen or fluid passageway. Increases in the local temperature may cause a movable element, for example a flap, of the bimaterial valve to expand or deflect allowing an increased volume of fluid to pass through the valve. The first and second materials 501, 502 are fixed on their outer periphery so that changes in temperature will not cause the outer edges to deflect. What is meant by "local temperature" is the temperature of an ablation cell in which a bimaterial valve is positioned and/or the temperature of an adjacent tissue. As the local temperature increases, the temperature of a fluid flowing through or present within the ablation cell may also increase. It should also be understood that a bimaterial valve may be constructed to cause a decrease in the flow rate of a flowable material in response to an increase in temperature by selecting an appropriate flap orientation and/or initial flap deflection.

The flap 503 may allow for a base-level fluid flow of between 0.5 mL/min and 2.5 mL/min, and preferably 1.5 mL/min, when the local temperature is at least about 37° C. and may expand or deflect as the local temperature increases allowing a greater volume of fluid to pass through the valve. For example, the flap 503 may be fully expanded or deflected when the temperature reaches at least about 90° C. to at least about 100° C. to allow a flow rate of between 10 mL/min and 20 mL/min, and preferably 16.5 mL/min. The bimaterial valve may also beneficially respond to pressure changes. For example, as the pressure increases, the bimaterial valve may expand or deflect to permit an increased volume of fluid to pass through the valve.

The thermal expansion coefficient of the first material 501 is preferably greater than the thermal expansion coefficient of the second material 502. The materials are preferably chosen such that the combination will exhibit deflection or expansion in response to changes in temperature, such deflection being caused by different coefficients of thermal expansion of each material and the fact that the two materials are fused together. Bimetallic deforming structures according to the present invention have predictable and repeatable flow states as a function of temperature of the structure, given a pressure head and upstream/downstream fluidic conductances.

In particularly preferred embodiments the first and second materials are rolled metal foils or films. For example, the first material 501 may comprise copper or a copper alloy and the second material 502 may comprise nickel, a nickel alloy, aluminum, or a steel. Other suitable combinations of metals include copper/gold, copper/Invar™, copper/Kovar™, copper/iron, copper/brass, copper/platinum, brass/gold, brass/nickel, brass/steel, brass/iron and brass/platinum. Non-metallic materials may also be used without departing the scope of the present invention, including distorting polymers, such as silicon, glasses and ceramics. A person of skill in the art would appreciate that any combination of materials that exhibit deflection or expansion in response to temperature changes may be used without departing from the spirit and scope of the present invention.

A bimaterial valve usable according to the present invention is not limited to the two-layer systems just described, but may include any number of layers, such as three-layers, four-layers, or more than for layers, that exhibit deflection or expansion in response to temperature changes. The invention requires only that flow-altering deformation is caused by a temperature change. The thermally-deforming materials, therefore, do not necessarily have to comprise the entire valve body or structure. For example, a deforming hinge made of a thermally-deforming material could swing a paddle made of a non-thermally deforming material. Bimaterial valves usable in accordance with the instant invention may be made from commercially available rolled metal-foil laminates. Such laminates may be obtained from vendors, such as Engineered Materials Solutions (EMS) of Attleboro, Mass.

A bimaterial valve usable according to the present invention is preferably circular or disc-shaped, but may have any suitable shape. In preferred embodiments, the bimaterial valve has a total thickness of about 0.005-0.030 inches, and preferably 0.020 inches, the first and second materials having a thickness of about 0.005-0.015 inches, and preferably 0.010 inches. The diameter of the valve is preferably approximately 10 to 100 times its total thickness. The bimaterial valve may be coated with a conversion coating or polymeric coating to improve corrosion resistance and/or biocompatibility. An example of a suitable coating is Parylene™ (Union Carbide). Such coatings may also contribute to useful valve thermal deformation.

In preferred embodiments, a bimaterial valve usable according to the present invention may be snapped into the desired location in a medical device either with or without the use of an adhesive. Alternatively, a bimaterial valve may be integrated within the device using a thermal or acoustic fusion process or a welding process. The bimaterial valve is preferably integrated in such a way to avoid flow leakage around the periphery of the valve.

Figure 7:
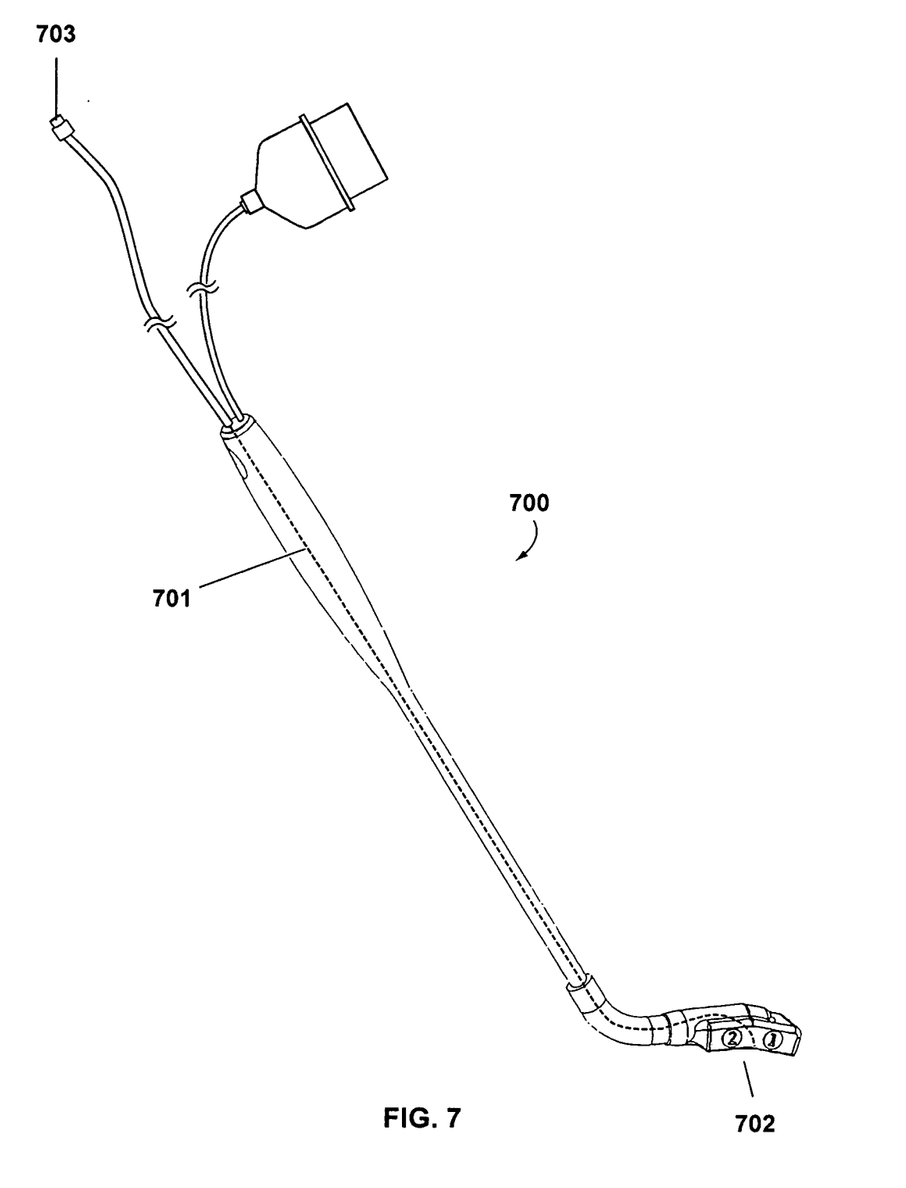
FIG. 7 depicts another embodiment of an ablation device according to the present invention having a single lumen feeding two ablation cells.
Figure 8:
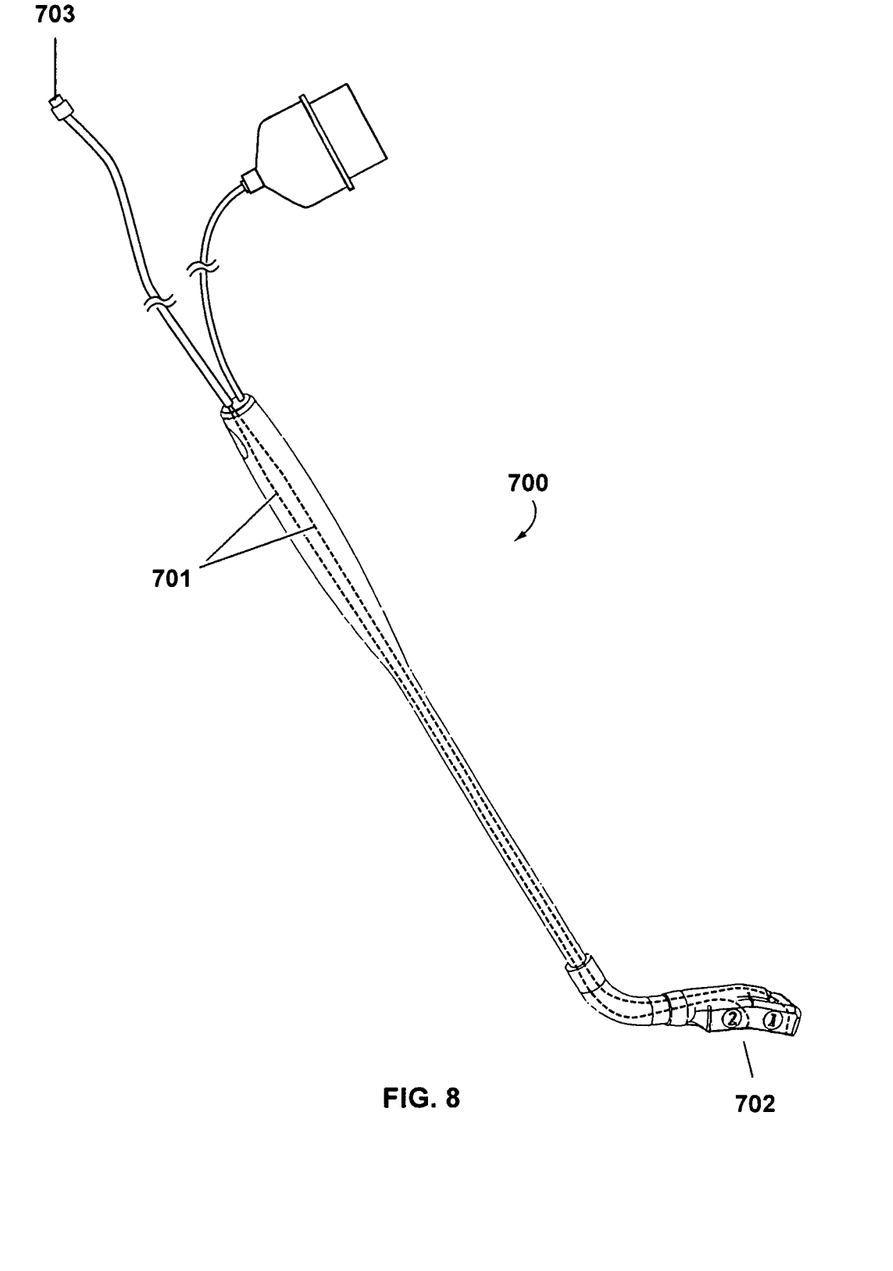
FIG. 8 illustrates the device of FIG. 7 having two lumens, each lumen feeding an individual ablation cell.

Referring to FIG. 7, another medical device for ablating tissue is shown. The device 700 includes a body having a fluid lumen 701. The device also includes at least one ablation cell and preferably two ablation cells 702, but may have any number of ablation cells. Each ablation cell may include an ablation element 106, a fluid passageway 107 and a bimaterial valve 108 positioned along the fluid passageway (see FIGS. 2A-B and 3A-B). Alternatively, the bimaterial valve may be integrated within the fluid lumen 701 near the fluid passageway of an ablation cell. The fluid lumen 701 may extend from a proximal portion of the device to the ablation cells 702 near a distal portion of the device and may be connected to a source of flowable material via a standard luer connector 703. In another preferred embodiment, the device may have two or more fluid lumens for carrying a flowable material and each fluid lumen may be connected to a single ablation cell (see FIG. 8). The device 700 may have any of the features previously described herein with respect to the devices of FIGS. 1 and 4.

A method of controlling the flow of a fluid is now described. A source of flowable material is connected to a medical device having at least one fluid lumen and at least one bimaterial valve, such as, for example, the devices previously described herein or any other suitable ablation device. The flowable material may be saline, hypertonic saline, or any other suitable fluid. The at least one bimaterial valve may control the flow of a fluid through the ablation cell in response to changes in temperature. The bimaterial valve may comprise a first material having a first thermal expansion coefficient and a second material bonded or fused to the first material having a second thermal expansion coefficient. The bimaterial valve may further include a movable element, such as a flap, that expands or deflects in response to temperature changes. As the temperature of the ablation cell or adjacent tissue increases, the temperature of the bimaterial valve may increase causing a movable element to expand or deflect, thus allowing a typically greater volume of fluid to flow through the valve. Some special applications may utilize flowable fluids which also perform other functions, such as blood, plasma, a drug, or saline or other fluid containing a drug.

Although several embodiments of this invention have been described above with a certain degree of particularity, those skilled in the art could make numerous alterations to the disclosed embodiments without departing from the spirit or scope of this invention. For example, although several ablation devices having multiple ablation cells or elements have been described in connection with the instant invention, it should be understood that other devices using a flowable material are known in the art and can be adopted for use according to the instant invention.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A device for ablating tissue comprising:
   at least one fluid lumen extending from a proximal end of the device towards a distal end of the device;
   at least one ablation cell positioned within a distal region of the device, the at least one ablation cell having an ablation element and a fluid passageway coupled to the at least one fluid lumen; and
   at least one bimaterial valve positioned along the at least one fluid lumen within the distal region of the device proximate at least one of: (a) the at least one ablation cell; and (b) a tissue adjacent the at least one ablation cell, for control of a fluid to the at least one ablation cell such that a flow rate of the fluid flowing from the at least one fluid lumen to the fluid passageway of the at least one ablation cell increases as a temperature of the at least one ablation cell or the tissue adjacent the at least one ablation cell increases.

2. The device of claim 1, wherein the ablation element is a high intensity focused ultrasound element.

3. The device of claim 1, wherein the at least one bimaterial valve comprises a first material having a first thermal expansion coefficient and a second material having a second thermal expansion coefficient bonded to the first material, and wherein the first and second materials are chosen such that the at least bimaterial valve has a first flow rate when the temperature is below a predetermined temperature and has a second flow rate when the temperature rises above the predetermined temperature, the second flow rate being greater than the first flow rate.

4. The device of claim 3, wherein the first material comprises copper and the second material is selected from the group consisting of nickel, aluminum, brass, steel, gold, iron and platinum.

5. The device of claim 3, wherein the first thermal expansion coefficient is greater than the second thermal expansion coefficient.

6. The device of claim 1, wherein the at least one bimaterial valve includes at least one flap that deflects with an increase in the temperature to increase a flow rate of the at least bimaterial valve.

7. The device of claim 1, further comprising a membrane enclosing the ablation element of the at least one ablation cell, the membrane and ablation element defining a fluid chamber therebetween.

8. The device of claim 7, wherein the membrane comprises at least one duct through which a fluid may flow.

9. The device of claim 1, wherein the at least one ablation cell comprises a plurality of ablation cells.

10. The device of claim 9, wherein the at least one fluid lumen comprises a single fluid lumen connecting to the plurality of ablation cells.

11. The device of claim 9, wherein the at least one fluid lumen comprises a plurality of fluid lumens, wherein each fluid lumen connects to a single ablation cell.

12. A device for ablating tissue comprising:
    at least one fluid lumen extending from a proximal end of the device towards a distal end of the device;
    at least one ablation cell positioned within a distal region of the device, the at least one ablation cell having an enclosure including an ablation element and a fluid passageway connected to the at least one fluid lumen,
    the at least one fluid lumen and the fluid passageway of the at least one ablation cell defining a fluid path; and
    at least one bimaterial valve positioned along the fluid path within the distal region of the device such that a flow rate of a fluid flowing through the fluid path to the at least one ablation cell exhibits a monotonic relationship to one or both of a temperature of the ablation cell and a temperature of an adjacent tissue.

13. The device of claim 12, wherein the flow rate is directly related to one of both of the temperature of the at least one ablation cell and the temperature of the adjacent tissue.

* * * * *